US007045134B2

(12) United States Patent
Qiu et al.

(10) Patent No.: US 7,045,134 B2
(45) Date of Patent: May 16, 2006

(54) BORELLIA BURGDORFERI EPITOPE PEPTIDES

(75) Inventors: Bo Qiu, East Brunswick, NJ (US); Guobao Zhang, Piscataway, NJ (US); Stanley Stein, East Brunswick, NJ (US); Leonard Sigal, Plainfield, NJ (US); Michael Brunner, Columbus, NJ (US); Michael Katz, Freehold, NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 328 days.

(21) Appl. No.: 09/982,259

(22) Filed: Oct. 17, 2001

(65) Prior Publication Data

US 2002/0197271 A1    Dec. 26, 2002

Related U.S. Application Data

(60) Provisional application No. 60/242,819, filed on Oct. 24, 2000.

(51) Int. Cl.
*A61K 39/02*    (2006.01)
*A61K 49/00*    (2006.01)
*A61K 39/08*    (2006.01)
*A61K 39/00*    (2006.01)

(52) U.S. Cl. .................. 424/190.1; 424/9.1; 424/9.2; 424/184.1; 424/185.1; 424/234.1; 435/41; 435/243; 530/300; 530/350

(58) Field of Classification Search .................. 424/9.1, 424/9.2, 184.1, 185.1, 190.1, 234.1, 8.2; 435/41, 243; 530/300, 360
See application file for complete search history.

(56) References Cited

U.S. PATENT DOCUMENTS

| 4,970,300 | A | 11/1990 | Fulton |
| 5,187,065 | A | 2/1993 | Schutzer |
| 5,219,564 | A | 6/1993 | Zalipsky |
| 5,455,027 | A | 10/1995 | Zalipsky |
| 5,545,698 | A | 8/1996 | Barany |

FOREIGN PATENT DOCUMENTS

| WO | WO 91 13630 | 9/1991 |
| WO | WO 97 42221 | 11/1997 |

OTHER PUBLICATIONS

Bar, Fritz W., et al., "New Biocompatible Polymer Surface Coating for Stents Results in a Low Neointimal Response," *J. Biomedical Materials Research* 2000; 52:193-198.
Becker, Timothy A., "Calcium Alginate Gel: A Biocompatible and Mechanically Stable Polymer for Endovascular Embolization," *J. Biomedical Materials Research* 2001; 54:76-86.
Buchko, Christopher J. et al., "Surface Characterization of Porous, Biocompatible Protein Polymer Thin Films," *Biomaterials* 2001; 22:1289-1300.
Buron, F., et al., "BOP: Biocompatible Osteoconductive Polymer: An Experimental Approach," *Clinical Materials* 1994; 16:217-221.
Ershov, I.A., et al., "Polymer Biocompatible X-Ray Contract Hydrogel for Esophageal Vein Obstruction in Portal Hypertension," *Med. Tekh.* 1994; 2:37-40. (Russian. See translation of Findings attached to article.).
Haisch, A., et al., "Tissue Engineering of Human Cartilage for Reconstructive Surgery Using Biocompatible, Resorbable Fibrin Glue with Polymer Structures," *HNO* 1996; 44:624-629. (German. English abstract on p. 625.).
Isobe, Masatsugu et al., "Bone Morphogenetic Protein Encapsulated with a Biodegradable and Biocompatible Polymer," *Journal of Biomedical Materials Research* 1996; 32:433-438.
Iwasaki, Yasuhiko et al., "Semi-interpenetrating Polymer Networks composed of Biocompatible Phospholipid Polymer and Segmented Polyurethane," *Journal of Biomedical Materials Research* 2000; 52:701-708.
Langer, R., "Biomaterials in Drug Delivery," *Accounts of Chemical Research.* Nov. 2, 2000; 33:94-101.
Langer, R., "Tissue Engineering," *Molecular Therapy* Jan. 2000; 1:12-15.
Polous, Y. M., et al., "The Application of the Biocompatible Antimicrobic Polymer Film for the Prevention of Intestinal Suture Incompetence Under Conditions of Peritonitis," *Vest. Khir. Im. II Grek* 1985; 134:55-57. (Greek. English abstract on p. 57.).
Qiu, Bo et al., "Selection of Continuous Epitope Sequences and Their Incorporation into Poly(Ethylene Glycol)-Peptide Conjugates for Use in Serodiagnostic Immunoassays: Application to Lyme Disease," *Biopolymers* 2000; 55:319-333.
Raudino, Antonio et al., "Binding of Lipid Vesicles to Protein-Coated Solid Polymer Surfaces: A Model for Cell Adhesion to Artificial Biocompatible Materials," *Journal of Colloid and Interface Science* 2000; 231:66-73.
Barbour, "The Biological and Social Phenomenon of Lyme Disease", 260 Science 1610 (1993).
Brunner, "Immune Complexes from Serum of Patients with Lyme Disease Contain *Borrelia burgdorferi* Antigen and Antigen-Specific Antibodies: Potential Use for Improved Testing", 182 J. of Infectious Diseases 534 (2000).

(Continued)

*Primary Examiner*—Rodney P Swartz
(74) *Attorney, Agent, or Firm*—Perkins Coie LLP (57) ABSTRACT

Immunologically invisible carrier molecules connect a plurality of copies of an immunologically active molecule in an immunologic assay.

14 Claims, 4 Drawing Sheets

OTHER PUBLICATIONS

Brunner, "Immunoglobulin M Capture Assay for Serologic Confirmation of Early Lyme Disease: Analysis of Immune Complexes with Biotinylated *Borrelia burgdorferi* Sonicate Enhanced with Flagellin Peptide Epitope", 36 J. Clin. Micro. 1074 (1998).

Brunner, "New Method for Detection of *Borrelia burgdorferi* Antigen Complexed to Antibody in Seronegative Lyme Disease", 249 J. Immunol. Methods 185 (2001).

Bückmann, "Functionalization of Poly(ethylene glycol) and Monomethoxy-Poly(ethylene glycol)", 182 Makromol Chem. 1379 (1981).

Ervin, "The Bell Tolls for the Infectious Diseases Clinician", 153 J Inf Dis 183 (1986).

Frank, "Spot Synthesis: An Easy Technique for the Positionally Addressable, Parellel Chemical Synthesis on a Membrane Support", 48 Tetrahedron 9217 (1992).

Geckeler, "Functionalization of Soluble Polymers", 1 Polym. Bull 427 (1979).

Geysen, "Use of Peptide Synthesis to Probe Viral Antigens for Epitopes to a Resolution of a Single Amino Acid", 81 Proc. Natl. Acad. Sci. 3998 (1984).

Gilmore, "Outer Surface Protein C (OspC), but not p39, is a Protective Immunogen Against a Tick-Transmitted *Borrelia burgdorferi* Challenge: Evidence for a Conformational Protective Epitope in OspC", 64 Infection and Immunity 2234 (1996).

Jungblut, "Proteomics in Human Disease: Cancer, Heart and Infectious Diseases", 20 Electrophoresis 2100 (1999).

Magnarelli, "Cross Reactivity of Nonspecific Treponemal Antibody in Serologic Tests for Lyme Disease", 28 J. Clin. Microbiol. 1276 (1990).

Mathiesen, "The Dominant Epitope of *Borrelia garinii* Outer Surface Protein C Recognized by Sera from Patients with Neuroborreloisis Has a Surface-Exposed Conserved Structural Motif", 66 Inf. And Immun. 4073 (1998).

Mathiesen, "Peptide Based OspC Enzyme-Linked Immunosorbent Assay for Serodiagnosis of Lyme Borreliosis", 36 J. Clin. Microbiol. 3474 (1998).

Qiu, "Studies on Polymers for Biomedical Applications: . . . ", (Dissertation, Oct. 1999) (unpublished).

Schneider, "Prognostic B-Cell Epitopes on the Flagellar Protein of *Borrelia burgdorferi*", 60 Inf and Immun. 316 (1992).

Sigal, "The Lyme Disease Controversy", 156 Arch. Intern. Med 1493 (1996).

Sigal, "Pitfalls in the Diagnosis and Management of Lyme Disease", 41 Arthritis & Rheumatism 195 (1998).

Sigal, "The Polymerase Chain Reactioon Assay for *Borrelia burgdorferi* in the Diagnosis of Lyme Disease", 120 Annals Intern. Med. 520 (1994).

Sigal, "A Vaccine Consisting of Recombinant *Borrelia burgdorferi* Outer-Surface Protein A to Prevent Lyme Disease", 339 New Engl. J. Med. 216 (1998).

Simpson, "Antibody to a 39-Kilodalton *Borrelia burgdorferi* Antigen (P39) as a Marker for Infection in Experimentally and Naturally Inoculated Animals", 29 J. Clin Microbiol 236 (1991).

Simpson, "Nucleotide Sequence and Analysis of the Gene in *Borrelia burgdorferi* Encoding the Immunogenic P39 Antigen", 119 Fed of Europ. Microbiol. Soc.s Letters 381 (1994).

Simpson, "Reactivity of Human Lyme Borreliosis Sera with a 39-Kilodalton Antigen Specific to *Borrelia burgdorferi*", 28 J. Clin Microbiol 1329 (1990).

Yu, "Multi-Well ELISA Based on Independent Peptide Antigens for Antibody Capture", 198 J. Immunol. Meth. 25 (1996).

Yu, "Presentation of Peptide Antigens as Albumin Conjugates for Use in Detection of Serum Antibodies by Enzyme-Linked Immunosorbent Assay", 7 Bioconjugate Chem. 338 (1996).

Zalipsky, "Attachment of Drugs to Polyethylene Glycols", 19 Eur. Polym. J. 1177 (1983).

Zalipsky, "Esterification of Polyethylene Glycols", A21 J Macromol. Sci.-Chem. 839 (1984).

Zalipsky, "Functionalized Poly(ethylene glycol) for Preparation of Biologically Relevant Conjugates", 6 Bioconjugate Chem. 150 (1995).

Figure 1. Synthetic scheme of poly(ethylene glycol) derived copolymer with multiple amino groups for peptide attachment.

Figure 2. Synthetic scheme of PEG-peptide conjugates containing multiple copies of peptides and reporter molecules Figure 3. Schematic description of PEG-peptide conjugates with reporter group on the N-terminus of the peptide Figure 4. IgM-capture ELISA using PEG-peptide conjugate as antigen for serological diagnosis of Lyme disease

BORELLIA BURGDORFERI EPITOPE PEPTIDES

CROSS REFERENCES

This application claims priority from Stanley STEIN et al., "Highly Sensitive and Specific IgM-Capture . . . ," provisional patent filing Ser. No. 60/242,819 filed 24 Oct. 2000 and Bo QIU et al., which is incorporated by reference in its entirety herein. The article by Bo QIU et al., "Selection of Continuous Epitope Sequences," 55 Biopolymers 319 (2001) is also incorporated here by reference.

GOVERNMENT RIGHTS

There are no Federal rights in this invention.

BACKGROUND

Current technology enables correct diagnosis of certain infectious diseases only after the disease has progressed to a certain maturity. By that time, however, treatment is more difficult. We have found a way to make disease diagnosis, even at an early stage, much more sensitive.

SUMMARY

Our invention entails presenting an immunologically reactive substance (e.g., epitope polypeptide) in multiple copies conjugated to an immunologically invisible carrier.

This basic conjugate has a variety of versions or embodiments. For example, while we do not prefer it, the epitope can be substituted or supplemented with any immunologically reactive substance such as an epitope, antigen (e.g., a polypeptide or nucleic acid) or antibody. Similarly, we prefer the carrier also connect a reporter moiety to make detection of the conjugate simpler.

The conjugate so made may then be used in a variety of ways. For example, we have shown it effective as part of an immunological assay. Alternatively, the conjugate may be used as a vaccine. Alternatively, the conjugate may be used as an in vivo therapeutic.

Thus, our basic idea can be used to make, for example, an immunological test kit. The term "immunological test kit" means a test kit which uses immune (e.g., antibody-epitope or antibody-antigen) interaction totest for the presence or absence of an analyte. Currently-known examples include ELISA, capillary immuno-chromatography and column immuno-chromatography. In making an immunologically test kit, it may be desirable to conjugate reporter moiety on the immunologically invisible carrier (e.g., polyethylene glycol). As another example, our basic idea can be used to conjugate several immunologically reactive substances (either several copies of the same substance, or copies of each of several different substances) together using an immunologically invisible carrier, which conjugate can be then used in an immunological test kit.

The immunologically reactive substance(s) can be one or more of the *Borellia burgdorferi* epitope polypeptides we discovered: VQEGVQQEGAQQP-(beta-A)(beta-A)C [SEQ ID NO: 1]; EIAAKAIGKKIHQNNG-(beta-A)(beta-A)C [SEQ ID NO: 2]; ISTLIKQKLDGLKNE-(beta-A)(beta-A)C [SEQ ID NO: 3]; PVVAESPKKPE (beta-A)(beta-A)C [SEQ ID NO: 4]; DKKAINLDKAQQKLD-(beta-A)(beta-A)C [SEQ ID NO: 5]; ITKGKSQKSLGD-(beta-A)(beta-A)C [SEQ ID NO: 6]; and GMTFRAQEGAFLTG-(beta-A)(beta-A)C [SEQ ID NO: 7]. Alternatively, one could use as antigen the nucleic acid coding for one or more of these epitopes. Using such an epitope enables one to make an apparatus for isolating anti-*Borellia burgdorferi* antibody (i.e., a Lyme disease test kit), a vaccine, or a therapeutic. Similarly, the nucleic acid sequences coding for these polypeptides may be useful as antigen, or to make large quantity of polypeptide.

Our basic idea can be made using, as an immunologically invisible carrier, a polyethylene glycol copolymer that we invented. It has the structure:

$$(-\!\!-\!\!NH-\!\!\text{polyethylene glycol}-\!\!NH-\!\!\overset{O}{\overset{\|}{C}}-\!\!\underset{NH}{\overset{|}{CH}}-\!\!CH_2-\!\!\overset{O}{\overset{\|}{C}}-\!\!)_r$$

We prefer using such a polyethylene glycol copolymer with the structure:

$$(-\!\!-\!\!NH-\!\!\text{polyethylene glycol}-\!\!NH-\!\!\overset{O}{\overset{\|}{C}}-\!\!\underset{\underset{\underset{\underset{\underset{R}{|}}{CH_2}}{|}}{\underset{\underset{O=S=O}{|}}{\underset{\text{polyethylene glycol}}{|}}}}{\overset{|}{CH}}-\!\!CH_2-\!\!\overset{O}{\overset{\|}{C}}-\!\!)_n$$

These are some of the many variations on our basic theme. In whatever variation, however, our invention ultimately requires presenting one or more immunologically reactive substances (e.g., epitope polypeptides) connected by an immunologically invisible carrier. We now discuss each of the components of our invention in turn.

IMMUNOLOGICALLY REACTIVE SUBSTANCE

Antibodies generally cannot bind to the whole antigen molecule. Rather, a specific antibody binds specifically to one individual epitope on that antigen. The term "immunologically reactive substance" means an epitope, an antigen or an antibody. To increase the specificity of our assay, we prefer to use not entire antigens, but one or more defined epitopes.

The success of a specific and sensitive immunoassay largely depends on the strength of antigen-antibody binding and the stability of the complex formed between the antigen and the antibody. The strength of antigen-antibody binding is measured by affinity, an intrinsic property of an antigen for a given antibody. To select an epitope peptide is to identify a peptide sequence with high affinity that can bind strongly with specific antibodies.

The stability of complex between antigen and antibody is measured by avidity, which is determined by three factors, the intrinsic affinity of the antibody for the antigen, the valence of the antibody and antigen, and the geometric arrangement of the interacting components. Thus, our invention works best when affinity, avidity and specificity (e.g., cross-reactivity) are used to first select an appropriate epitope(s). After the specific epitopes are selected, they can be made as desired (e.g., purified from natural protein or synthesized).

The sensitivity of an immunoassay relies on providing enough of each epitope and on having the right orientation and conformation of the epitope. Thus, we prefer the epitope peptides be modified as necessary to assume the right orientation and conformation to obtain a strong antigen-antibody binding.

Whole antigen or antibody may be used instead of epitope, to mount to the carrier molecule. If mounting antibody on the carrier, the antibody-carrier complex can be used to trap antigen epitope analyte in the test solution.

Multiple Copies

Epitopes are specific, but have a key shortcoming. The affinity of epitope peptides to anti-protein antibodies can be 100 to 1,000 times weaker than that of the whole antigen (whole protein). Thus, the affinity between a single epitope and the serum antibody might not be strong enough to endure the vigorous washing steps in an immunoassay.

To address this problem, we use multiple copies of each epitope, connected together with a "carrier." Connecting multiple copies of epitope peptides enable the epitopes to form multivalent interactions between two or more Fab fragments of the antibody. This creates a synergistically greater binding strength. More specifically, binding strength increases, perhaps exponentially, with the number of additional copies of epitope connected to the carrier.

For example, an epitope alone may have an antibody affinity 100 times weaker than the native antigen. The same epitope, however, if provided in pairs (i.e., two copies of the epitope connected together), might have affinity only 10 times weaker than the native antigen. Further, the same epitope provided in trios (i.e., three copies of the epitope connected together) might have native-strength affinity. We believe this effect especially true where the target antibody is IgM, itself a pentamer.

Immunologically Invisible Carrier

We call the material that connects the various copies of the epitope a "carrier" molecule. Any molecule that can bind more than one copy of an epitope can function as a "carrier." Examples include keyhole limpet hemacyanin, albumins such as serum albumin (e.g., bovine serum albumin, mouse serum albumin, rabbit serum albumin) and ovalbumin, and polyethylene glycol derivatives. These materials can each bind multiple copies of an epitope.

Of these carriers, however, most are unsuitable because they are immunologically "visible," that is to say, they react in an immunological test (even without epitope present) to create a statistically significant increase in (sometimes random) background reactivity. Albumin and limpet hemacyanin tend to stick to ELISA plates. Thus, when using these proteins as carriers, the carrier itself adheres to the ELISA plate in quantity sufficient to cause an elevated background. This problem is particularly significant in developing diagnostic assays for disease where the serum antibody level is relatively low and the signals thus barely detectable. The elevated background compromises the signals, ruining the assay sensitivity and specificity.

Our invention is thus limited to "immunologically invisible" carriers. Excluded from the term "immunologically invisible" are full length albumins and keyhole limpet hemacyanin, because these are not immunologically "invisible."

Biocompatible Polymers

Immunologically invisible carriers are carriers which do not generate statistically significant background immunological reactivity. Immunologically invisible carriers include, for example, biocompatible polymers.

Such polymers are known in the art. General reviews of such compounds include Langer, R., "Biomaterials in Drug Delivery," 33 Acc. Chem. Res. 94 (2000); and Langer, R., "Tissue Engineering," 1 Mol. Ther. 12 (2000). One example of such an immunologically invisible compound is a N-vinylpyrrolidone-methyl methacrylate co-polymer, perhaps with added polyamide-6. Buron, F. et al., *Biocompatable Osteoconductive Polymer*, 16 Clin. Mater. 217 (1994). Another example is poly (DL-lactide-co-glycolide) capsules. Isobe, M. et al., *Bone Morphogenic Protein Encapsulated with a Biodegradable and Biocompatible Polymer*, 32 J. Biomed. Mater. Res. 433 (1996). Mother example is a 70:30 ratio mixture of methylmethacrylate:2-hydroxyethyl methacrylate. Bar, F. W. et al., *New Biocompatable Polymer Surface Coating*, 52 J. Biomed. Mater. Res. 193 (2000). Another example, is 2-methacryloyloxyethyl phosphorylcholine, perhaps with polyurethane. Iwasaki, Y. et al., *Semi-Interpenetrating Polymer Networks . . .* , 52 J. Biomed. Mater. Res. 701 (2000). Polyvinyl pyrrolidone may also be used, as may polyethylene glycol and its derivatives. Other biocompatible polymers are known in the art. E.g., Haisch, A. et al., *Tissue Engineering of Human Cartlage Tissue*, 44 HNO 624 (1996); Ershov, I. A. et al., *Polymer Biocompatible X-Ray Contract Hydrogel*, 2 Med. Tekh. 37 (1994); Polous, I. M. et al., *Use Of A Biocompatible Antimicrobial Polymer Film*, 134 Vestn. Khir. Im. II Grek. 55 (1985).

In addition to such synthetic polymers, immunologically invisible biological materials may be used. An example is calcium alginate, such as purified high guluronic acid alginates. Becker, T. A. et al., *Calcium Alginate Gel,* 54 J.Biomed.Mater.Res. 76 (2001). Genetically engineered protein polymers also may be acceptable. Buchko, C. J. et al., *Surface Characterization of Porous, Biocompatible Protein Polymer Thin Films,* 22 Biomaterials 1289 (2001); cf. Raudino, A. et al., *Binding of Lipid Vescicles . . .* , 231 J.Colloid.Interface Sci. 66 (2000).

Such compounds may lack functional groups useful for attaching the desired immunologically reactive substance to the carrier. Thus, it may be desirable to use not the pure polymer, but a co-polymer having appended functional groups. The functional groups may then be filled with the desired immunologically reactive substance.

As immunologically invisible carrier, we prefer polyethylene glycol and its derivatives. We thus now discuss it in some detail.

Polyethylene Glycol

Polyethylene glycol (often simply called "PEG") is a water soluble, non-immunogenic, biocompatible material.

When used as a carrier, the useful properties of polyethylene glycol with respect to the appended moiety include improved solubility, increased circulation lifetime in bloodstream, resistance to proteases and nucleases, etc. The large molecular weight of polyethylene glycol makes it very easy to separate the final conjugates from excess epitope peptide and other small-size impurities. Polyethylene glycol does not aggregate, degrade or denature. Polyethylene glycol conjugates are thus stable and convenient for use in diagnostic assays.

While the polyether backbone of polyethylene glycol is chemically inert, the primary hydroxyl groups on both ends are reactive and can be utilized directly to attach immunologically reactive substances. These hydroxyl groups have been transformed into more reactive functional groups for conjugation purposes. Such polyethylene glycol derivatives possess only two functional groups on the ends. This limits the number of conjugations to just two. We thus prefer a polyethylene glycol derived polymer system with multiple functional groups for epitope peptide attachment.

We made a new polyethylene glycol with multiple functional groups and a favorable geometric arrangement to achieve strong and stable antigen-antibody blinding for the selected epitope peptides. We used α,ω-diamino-polyethylene glycol to copolymerize with amino group-protected aspartic acid to obtain a new polyethylene glycol-aspartic acid copolymer. Multiple attachment sites become available for conjugation through the pendant amino groups of the aspartic acid residue upon removal of the protection (FIG. 1).

To allow the attached epitope peptides to assume a favorable geometric arrangement for antibody binding, we used a long arm cross-linker for attaching the epitope peptides to the amino groups, so that the attached epitope peptides can be positioned far enough from the polymer backbone to avoid steric hindrance. We used a heterobifunctional polyethylene glycol-based cross-linker, NHS-polyethylene glycol-VS, as the cross-linker for epitope peptide conjugation.

The conjugation of epitope peptides may use thiol-specific chemistry under mild conditions. The easiest strategy for peptide conjugation is to add an extra amino acid on either the amino or carboxyl terminus of the peptide to allow one-site coupling to the carrier. In our study design, a cysteine residue, followed by two β-alanine residues, was incorporated at the C-terminus of each epitope peptide during solid phase peptide synthesis. Putting two more β-alanine residues between the conjugation anchor, cysteine, and the epitope peptide is used as a precaution to generate further flexibility of the linear peptides, and therefore help them to adopt the optimal conformations for stronger antibody binding. The N-terminus of the peptides needs to be capped in order to remove charges associated with free amino groups and thereby mimicking the real environment in the protein.

To conjugate epitope peptides to the polymer backbone, a two step approach can be used. A heterobifunctional cross-linker, NHS-polyethylene glycol-VS can first react with the reserved amino groups in the reporter-labeled polymer carrier through, the NHS groups. After purification to remove excess cross-linker, cysteine-containing epitope peptides can then react readily with vinylsulfone groups (VS) to complete the conjugation. The final polyethylene glycol-peptide conjugates containing multiple copies of epitope peptides and several copies of reporter molecules are now ready for immunoassays (FIG. 2).

Reporter

The carrier-epitope conjugates may be labeled by, for example, washing with labeled anti-epitope antibody. Alternatively, a label or "reporter" moiety may be conveniently included in the carrier-epitope conjugates; this allows for a one-step (rather than a two-step) detection process. The construction of such carrier-epitope conjugates involves two aspects: the conjugation of reporter molecules, and the conjugation of epitope peptides.

A commonly used reporter molecule in immunoassay is biotin. Its corresponding N-hydroxysuccinimide ester (NHS) with extended spacer is chosen for our carrier-peptide conjugate preparation. We did this because the NHS group can react readily with the pendant amino groups of the polyethylene glycol-aspartic acid copolymer under mild conditions. The extended spacer arm can help lower steric hindrance and thus facilitate assay detection. Since biotin detection system is extremely sensitive, a few label molecules should suffice to give satisfactory signals. Therefore, only a small portion of attachment sites in the carrier is needed to attach reporter molecules so that a large portion of the attachment sites can be reserved for the epitope peptides to generate polyvalent antigen with improved antibody binding and to improve the sensitivity of the immunoassay.

Alternatively, the reporter molecule can be put on the N-terminus of the epitope peptides during the solid phase peptide synthesis. The reporter molecules can thus serve as the capping groups of the peptides and as the reporter groups of the conjugates simultaneously. By putting the reporter groups both on the polymer backbone and on the epitope peptides, the assay signal can be further enhanced (FIG. 3). Care must be taken to not block the epitope from contacting and binding to the antibody. Multiple copies of the reporter groups attached to the carrier amplify the assay signal. Other reporters or labels (e.g., colloidal metal, carbon black, latex beads) are known in the art and may alternatively be used.

Uses

Once made, our carrier-epitope conjugates can be used for a variety of things. For example, our conjugates can be used in immuno-chromatography, the specific kind of chromatography selected depending on one's goals. Column chromatography, for example, can be done with our conjugates used to isolate and purify a desired antibody in quantity. Alternatively, capillary chromatography can be done with our conjugates, to detect low levels of antibody in a sample. Similarly, ELISA can be done with our conjugates, to detect low levels of antibody in a clinical sample. We actually used our conjugates to make such an immunodiagnostic kit, so we will now discuss how to make such a kit in some detail.

DETAILED DESCRIPTION OF OUR PREFERRED EMBODIMENT

Our preferred embodiment of our invention entails four parts: 1) the selection of specific epitopes by epitope mapping; 2) the design and synthesis of a carrier molecule with multiple attachment sites; 3) the preparation of multivalent carrier-peptide conjugates with one or more reporter groups; and 4) the use of the prepared carrier-peptide-reporter conjugates in an immunological assay. Here is how you can use our preferred embodiment to make an indirect IgM-capture ELISA effective for the diagnosis of Lyme disease at its earliest state.

Epitope Mapping by SPOTS

All concurrent peptide sequences were generated using computer software provided by the manufacturer (Genesys)

with the SPOTS kit. By providing a protein sequence, desired length of each peptide and offset of amino acids for each peptide, the program can edit peptide sequences to be assembled on SPOTS membrane and provide the amino acid addition schedule for each synthesis cycle.

To start the peptide synthesis on the membrane, pre-weighed Fmoc-amino acid active esters were dissolved in DMF and pipetted to appropriate spots on the membrane based on the generated synthesis schedule. Double coupling was done for each cycle to ensure the completion of the reaction. All the Fmoc-amino acid active esters, except Arginine, are relatively stable and can be dissolved in DMF for use of several cycles in the same working day, as long as they are stored at −20° C. between each addition. Due to its intrinsic instability, the Fmoc-Arginine active ester must be dissolved just before use and a fresh aliquot must be used for each coupling cycle. The initial color of all spots on the membrane was blue which is produced by bromophenol blue in the presence of the free amino groups on the de-protected amino acids.

As coupling proceeds with the addition of Fmoc-amino acid active esters, the spots change to different colors for different amino acids. For example, Asparagine and Threonine change to green, Serine changes to yellow. The color change can be regarded as a sign that the coupling is taking place. After coupling an amino acid the membrane was washed 3×20 mL DMF for 2 minutes each time to remove excess active esters.

Then, acetic anhydride was added to acetylate any uncoupled amino groups to ensure no formation of deletion sequences. As all free amino groups are capped by acetylation, the remaining blue color disappeared. The membrane was washed 3×20 mL DMF and then 20 mL of 20% piperidine in DMF was added to remove Fmoc protecting groups. After washing membrane 5×20 mL DMF, 200 µL of 1% bromophenol blue solution was added to 20 mL DMF and this solution was added on the membrane. Due to piperidine removal of the Fmoc groups, the spots turned blue leaving the surrounding membrane white and the solution yellow. The membrane was washed 3×20 mL with methanol. After air drying on a sheet of folded filter paper, the membrane is ready for the next coupling cycle. This procedure was repeated for all but the final coupling cycle of the synthesis.

For the final cycle, piperidine treatment was carried out right after the double coupling of active esters and DMF washing. Bromophenol blue solution was then added to obtain blue color for all spots and finally the peptides on each spot were capped by acetylation. After synthesis and acetylation, the protecting groups present on the side chains of the amino acids must be removed. For side chain deprotection, 5 mL of DCM was mixed with 5 mL TFA. The mixed solution was added immediately onto the air-dried membrane and the cleavage reaction was allowed to proceed for 1 hour. The membrane was then washed with 3×20 mL DCM, 3×20 mL DMF, and 3×20 mL methanol. The membrane was air-dried and stored in a sealed plastic bag in the freezer (−20° C.) until required for SPOTS analysis.

For analysis, the SPOTS membrane was first blocked with 20 mL of TBS-blocking buffer overnight at room temperature. The membrane was washed with 20 ml; Tris buffered saline (TBS) containing 0.05% Tween-20 (T-TBS). The serum sample (Lyme disease or control) was diluted in 20 mL TBS-blocking buffer to 1:100. This diluted test antibody solution was added to the membrane and rocked for 3–4 hours at room temperature. The membrane was washed with 3×20 mL T-TBS for 10 minutes each wash. Then, 100 µL of P-galactosidase conjugated anti-human (G+M+A) secondary antibody was diluted with 20 mL of TBS-blocking buffer. This was added to the membrane and rocked for 2 hours at room temperature.

During this time, the signal development solution was prepared as follows: Dissolve 4.9 mg BCIG in 100 µL DMF and 100 mg potassium ferricyanide in 1 mL MilliQ water. Add BCIG solution and 100 µL of potassium fenicyanide solution into 10 mL of phosphate buffered saline (PBS) containing 10 µL of 1 M magnesium chloride solution. After the incubation of the secondary antibody solution, wash the membrane 2×20 mL T-TBS followed by 2×20 mL PBS, then add the prepared signal development solution to the membrane and rock at room temperature until blue spots appear. Allow the color to develop for 40 to 50 minutes until a point at which there is a clear distinction between positive and negative spots. Pour off the signal development solution and wash the membrane with 2×20 mL PBS. Photograph the stained membrane to provide a permanent record.

The SPOTS membrane must be regenerated after analysis of each serum sample to remove bound proteins before storage or regarding-probing. To regenerate the membrane, it was washed with 5×20 mL MilliQ water and then 3×20 mL DMF followed by another 2×20 mL MilliQ water. Then, 20 mL, of regeneration buffer A (485.0 g urea, 10.0 g. SDS and 1 mL 2-mercapteotbanol in 1 L of MilliQ water) was added and the membrane was incubated for 10 minutes at room temperature. The process was repeated twice. Then 20 mL of regeneration buffer B (Mix 400 mL of MilliQ water and 500 mL ethanol, add 100 mL of acetic acid to above solution) was added and the membrane was incubated for 10 minutes at room temperature. The process was repeated twice. Finally, the membrane was washed with 2×20 mL methanol and air-dried. The membrane was stored in a sealed plastic bag in the freezer (−20° C.) until the next analysis.

Synthesis, Purification and Characterization of Epitope Peptides

All 7 epitope peptides (Table 1) were synthesized manually on PAL™ resin (0.34 mmol/g, 0.1–0.2 mmol scale) in a polypropylene column (Bio-Rad Laboratories, Herculus, Calif.). DMF (3 ml) was added to swell the resin for 20 min. After Fmoc deprotection with 20% piperidine in DMF for 2×20min, the resin was rinsed with 3 ml of DMF three times, 3 ml of methanol three times, then dried in air. The coupling was achieved by adding 3-fold molar excess of each amino acid, mixed with equimolar amounts of BOP and HOBt in 3 ml of DMF containing 1% (v/v) DHEA. Coupling proceeded at room temperature for 4 hours.

After coupling, the resin was washed with DMF and methanol and air-dried. A sample of the resin was tested with Kaiser ninhydrin reagent (1:1:1 v/v/v 0.2 mM KCN in pyridine, 4 mg/ml of phenol and 5% ninhydrin in butanol) at 10° C. for 3 min (Kaiser et al., 1970; Sarin et al., 1981). If the resin showed blue color, double coupling would be conducted for another 4 hours to drive the reaction to completion. The resin was capped using 4 mL of DMF, 400 µL of acetic anhydride and 80 µL of triethylamine for 4 hours to eliminate any un-reacted amino groups.

The coupling procedure was repeated until the desired peptide sequence was obtained. (See Table 1 for the seven synthesized peptides.) When the assembly of the peptide sequence was complete, the N-terminus of all epitope peptides was capped with long chain biotin to serve the two purposes simultaneously. The first purpose is to remove the charge associated with the free amino group of the N-terminus, thus to mimic the real environment in the natural protein sequence. The second purpose is to use the biotin as the detection label for biotin-avidin binding in ELISA.

TABLE 1

Synthesized Epitopes

| Peptide | Sequence | |
|---|---|---|
| FLA, AA 211-223 | VQEGVQQEGAQQP-(beta-A)(beta-,4)C [SEQ ID NO: 1] | 1639.8 |
| OspC2, AA71-86 | EIAAKAIGKKIHQNNG-(beta-A)(beta-A)C [SEQ ID NO: 2] | 2274.3 |
| OspC3, AA 104-118 | ISTLIKQKLDGLKNE-(beta-A)(beta-A)C [SEQ ID NO: 3] | 2282.3 |
| OspCIO, AA 198-207 | PWAESPKKPE-(beta-A)(beta-A)C [SEQ ID NO: 4] | 1762.7 |
| P83-1, AA296-310 | DKKAINLDKAQQKLD-(beta-A)(beta-A)C [SEQ ID NO: 5] | 2310.3 |
| P83-3, AA 43 1-442 | ITKGKSQKSLGD-(beta-A)(beta-A)C [SEQ ID NO: 6] | 1843.8 |
| P39, AA129-142 | GMTFRAQEGAFLTG-(beta-A)(beta-A)C [SEQ ID NO: 7] | 2067.9 |

Long chain biotin was selected to reduce any possible conformational hindrance for high-avidity biotin-avidin binding. All peptides were cleaved from the resin with trifluoroacetic acid (TFA)/thioanisole/ethanedithiol (EDT)/anisole (90/5/3/2%, v/v) at 1 mL/100 mg resin for 2 hours at room temperature. The cleavage mixture was filtered through glass wool, which was then rinsed with TFA twice. The filtrates were combined and evaporated under an Argon stream to reduce the volume to about 1–2 mL, then precipitated by adding drop-wise into 10 times volume of ice-cooled diethyl ether. The white precipitate was washed with cold diethyl ether five times to remove scavengers. Crude peptides were purified by reverse phase HPLC under acidic condition (0.1% TFA), because cysteine was incorporated in all epitope peptides for conjugation purpose and the availability of free thiol groups in cysteine is critical for conjugating epitope peptides onto PLC copolymer backbone. The acid condition can help to prevent or minimize the oxidation of the free thiol groups. After HPLC purification, the tubes containing the epitope peptides were flushed with Argon stream, capped, wrapped with paraffin, and stored dry in the refrigerator (4° C.). The purified epitope peptides were characterized by amino acid analysis and mass spectrometry.

Synthesis and Purification of Polyethylene Glycol-Aspartic Acid Copolymers

Amino group protected L-Aspartic acid (Boc-Asp-OH) (BACHEM, King of Prussia, Pa.) and α,ω-diamino-PEG (NH2-PEG-NH2, Shearwater Polymers, Huntsville, Ala.) were copolymerized based on carbodiimide reaction in the presence of 4-(dimethyl amino)-pyridine (DMAP) and p-toluenesulfonic acid monohydrate (PTSA) as catalysts. In a typical preparation, NH2-PEG-NH2 (680 mg, 2×10 mol) and Boc-Asp-OH (46.6 mg, $2 \times 10^{-4}$ mol) were dissolved in 20 mL methylene chloride with stirring. DMAP (12.2 mg, $1 \times 10^{-4}$ mol) and PTSA (19.0 mg, $1 \times 10^{-4}$ mol) were added. To this solution 1,3-diisopropylcarbodiimide (DIPC) (15.6 mL, $1 \times 10^{-3}$ mol) was added at 0° C. under stirring. The reaction flask was sealed with a rubber stopper assembled with an Argon balloon. The reaction was allowed to continue at room temperature with stirring until the reaction mixture became viscous.

The reaction mixture was precipitated in 10 volumes of ice-cold ethyl ether to obtain the white polymer product. The polymer was washed three times with ice-cold ethyl ether and the polymer product was collected by filtration or centrifugation. The polymer was dried under an Argon flow, redissolved in MilliQ water and purified by dialysis using Spectra/For™ Spectrum cellulose ester membrane (MW 12-14,000 Da) for 24 h. After lyophilization, the polymer was treated with TFA for 3 hours to remove all the Boc protecting groups. The de-protected polymer solution was then precipitated in 10 volumes of ice-cold ethyl ether, washed three times with ice-cold ethyl ether and dried under vacuum. The molecular weight of the resulting PEG copolymer was measured by size exclusion chromatography.

Preparation of Polyethylene Glycol-Peptide Conjugates

To a solution of PEG copolymer in 50 mM carbonate-bicarbonate buffer (pH=8.5) was added 0.5 equivalent (relative to the amino groups in the polymer) of NHS-LC-Biotin in DMSO. The mixture was stirred at room temperature under Argon overnight. After about 10 hours of reaction, approximately 30% of the amino groups in the PEG, copolymer were reacted and linked to biotin molecules. A fluorometric assay, using a fluorogenic reagent, Fluram, was employed to check the extent of the biotinylation reaction. In brief, 100 μL of PEG copolymer solution was saved before adding the biotinylation reagent and diluted 10× in 0.2 M borate buffer, pH 8.5) as reference. When reaction was complete, 100 mL of reaction mixture was taken and diluted 10× in 0.2 M borate buffer (pH 8.5) as sample.

For fluorometric assay, 50 mL of Fluram solution (15 mg Fluram dissolved in 25 mL acetonitrile) was added to 150 μL of diluted reference, 150 μL of diluted sample and 150 μL of blank (0.2 M borate buffer, pH 8.5), respectively, in separate wells of a microtiter plate. After mixing immediately by pipetting up and down several times, fluorescence was read on a Fluorescence Multi-Well Plate Reader (CytoFluor™ 11, PerSeptive Biosystems) with the excitation wavelength set at 400 nm and the emission wavelength set at 460 nm. The biotin labeled PEG copolymer was purified by a Pharmacia Superdex-75 column and then reacted with 3 molar equivalents of hetero-bifunctional NHS-PEG-VS (MW 2000 Da), relative to free amino groups remaining in biotin-labeled PEG copolymer.

The latter reaction, which was also monitored by the fluorometric assay, was complete after 4 hrs at room temperature (25° C.). The fluorometric assay procedure was similar to that described above. The final fluorescence reading was equal or close to the blank reading, suggesting that (all amino groups in the PEG copolymer had been successfully derivatized. The reaction product was purified through a Pharmacia Superdex-75 column or by membrane dialysis. For peptide conjugation, 5 molar equivalents of peptide relative to the available vinylsulfone (VS) groups in the PEG copolymer were added to the activated polymer solution, and these were allowed to react at 4° C. overnight. The final Biotin-PEG-peptide conjugate was purified by the Pharmacia Superdex-75 column or by membrane dialysis, and concentrated to about 1 mg/mL using a Centricon™ ultrafilter (mw 10,000 Da). Aliquots were stored as the stock antigen solution in the freezer (−20° C.) until needed.

The Enzyme-Linked Immuno-Sorbent Assay

ELISA is a simple but very sensitive immunoassay. It involves the following basic steps: An antigen is bound to a solid phase material, usually a 96-well plastic plate. The solution containing the antibody to be detected (usually serum) is added to the well having the immobilized antigens. Unrelated, unbound antibody is then washed away. A second antibody, which is an anti-immunoglobulin antibody linked with an enzyme, is then added to the wells. Then the substrate for the enzyme is added to the above reaction mixture and the amount of enzymatically altered substrate is measured. The enzyme and substrate are chosen so that enzymatic modification of the substrate produces a change in color of the substrate solution. The amount of changed substrate (which may be measured with a spectrophotometer) is proportional to the amount of antibody bound to the immobilized antigen.

There are generally two types of ELISA formats: direct and indirect. In a direct ELISA, antigens first bind to the well surface of the plates, and then the bound antigens interact with the test antibodies and give the signals. In an indirect ELISA, the plates are first coated with antibodies that can capture antigens. The captured antigens can then interact with the test antibodies and give the signals.

Many modifications of the above basic technique can be used depending on the nature of the sample, availability of reagents and the precision and sensitivity required. For example, one may use a biotinylated antibody followed by enzyme-conjugated avidin or streptavidin. The avidin-biotin method results in an amplified effect since many biotin molecules may be attached to a single second antibody molecule and multiple avidin molecules can then bind subsequently to the second antibody. For this reason, the avidin-biotin method is particularly sensitive.

i) IgM Capture ELISA

In an IgM-capture format, IgM antibodies are captured or bound to the test support, such as an ELISA plate. A representative portion of all IgM antibodies, including disease specific and unrelated IgM antibodies, are captured. All other classes of antibodies are removed.

In a direct-capture test, the antigens are immobilized on the surface of the plate. In an indirect-capture test, the antigens are present in the test solution and interact with the antibodies captured or bound to the ELISA plate.

Figure 1:
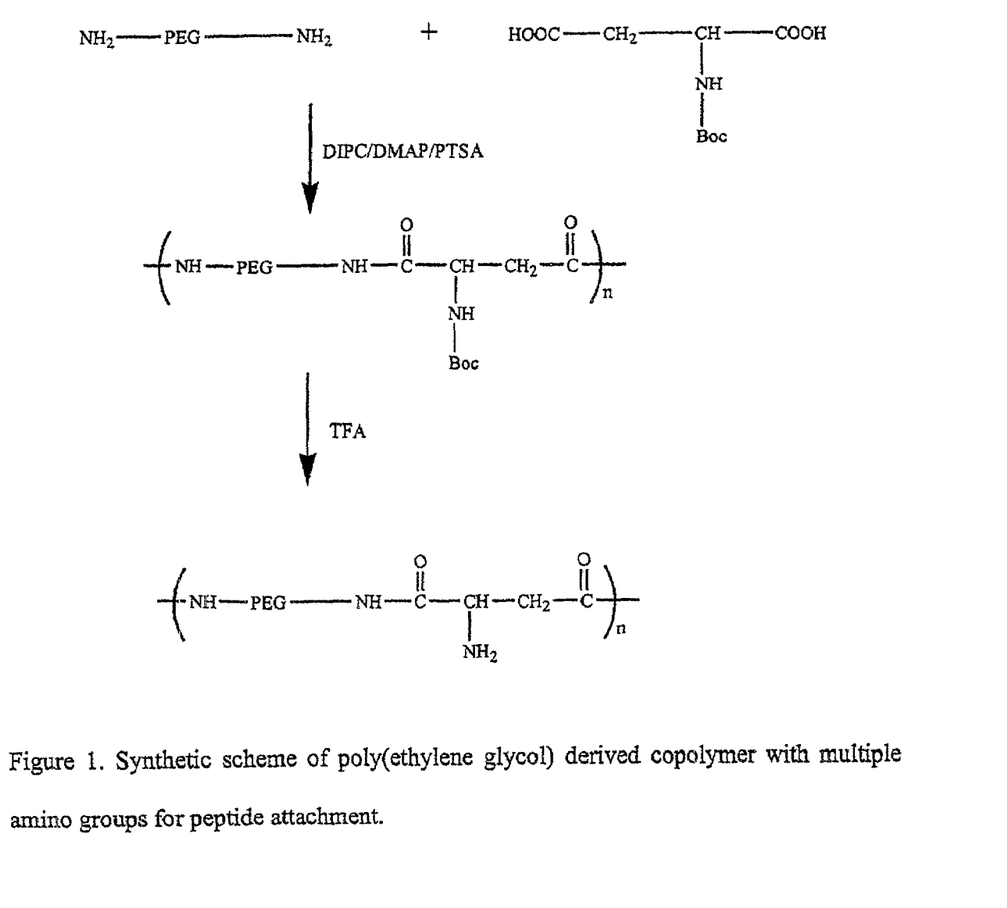
FIG. 1 shows the synthesis of a polyethylene glycol-derived copolymer, which has multiple amino groups capable of attaching peptides to the copolymer.
Figure 2:
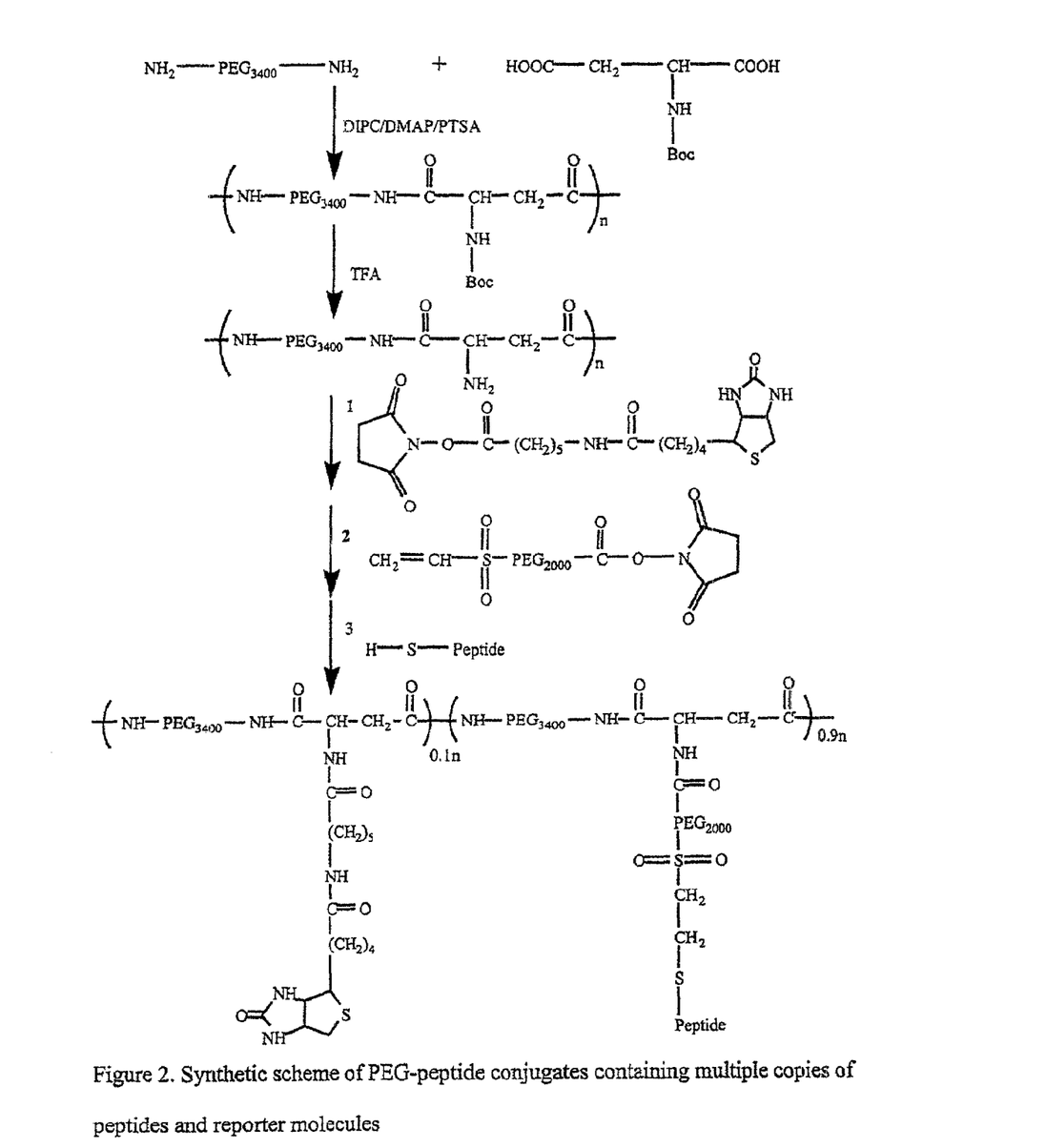
FIG. 2 shows the synthesis of polyethylene glycol (PEG) and peptide conjugates, which contain multiple copies of peptides and reporter molecules.
Figure 3:
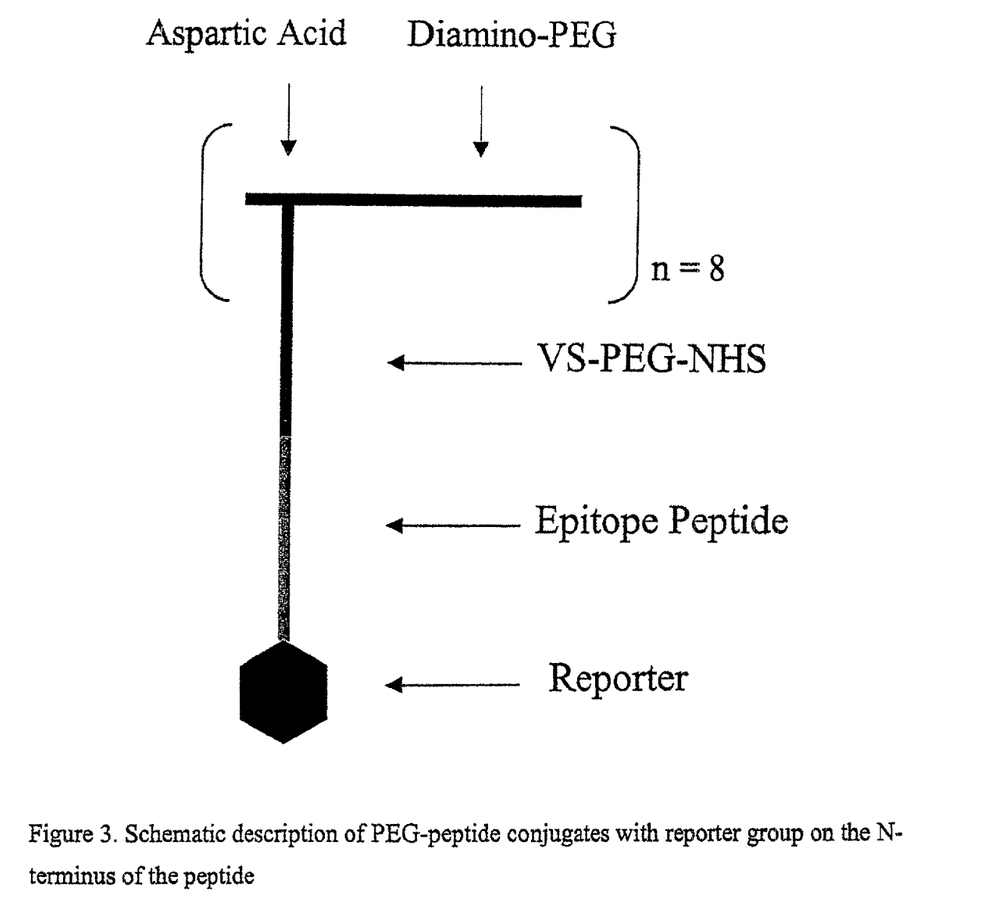
FIG. 3 is a schematic representation of a PEG-peptide conjugate with a reporter group attached to the N-terminus of the peptide.
Figure 4:
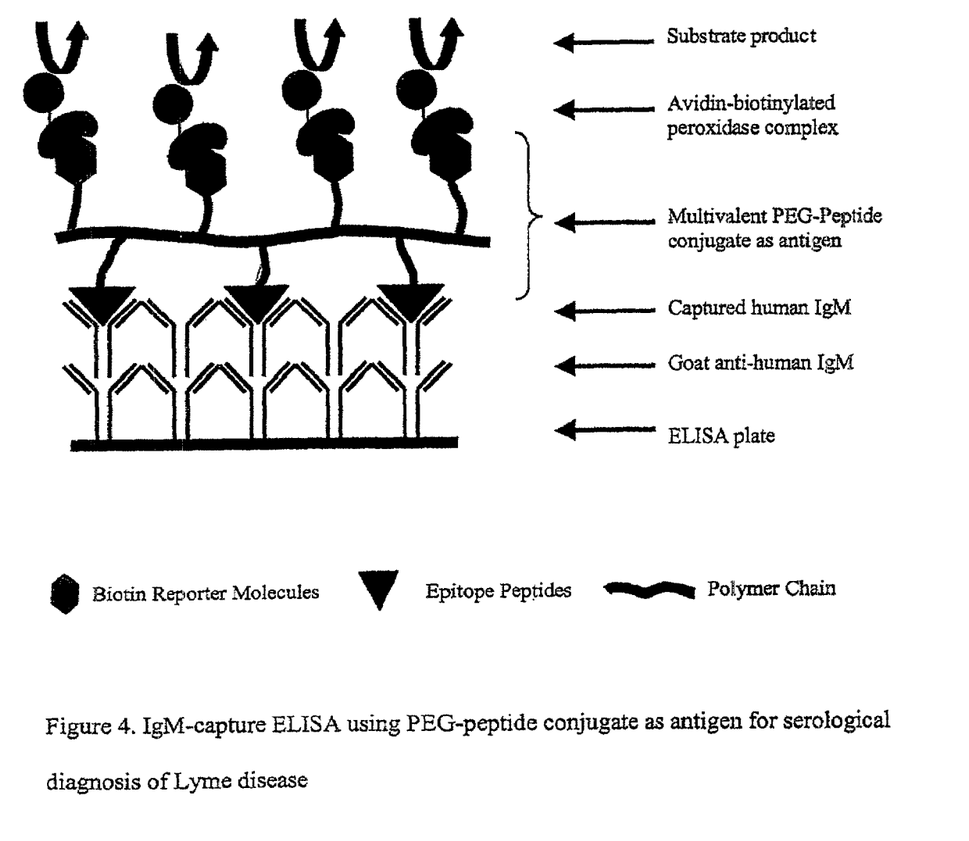
FIG. 4 is a cartoon representation of IgM-capture ELISA using PEG-peptide conjugate as antigen for serological diagnosis of Lyme disease.

When the captured IgM antibodies are exposed to the prepared PEG-peptide conjugates, these Lyme disease specific epitope conjugates will only bind to Lyme disease specific IgM antibodies. If no Lyme disease specific IgM antibodies are present, all conjugates will be washed away and no signal can be detected. As a result, a negative result is obtained. Clearly, this indirect IgM capture ELISA format, combined with using the Lyme disease specific conjugates as antigens, increases the sensitivity and the specificity of detecting Lyme disease specific IgM antibodies, on which a highly sensitive and specific immunoassay can be developed (FIG. 4).

ELISA plates were coated with 100 μL/well of affinity-purified goat anti-human IgM antibody (10 μg/mL) in 0.04 M carbonate-bicarbonate buffer, pH 9.6. Plates were slowly rotated on a Titer Plate Shaker (Lab-Line, Melrose Park, Ill.) for 2 h at room temperature, and kept at 4° C. overnight. The plates were washed three times in a plate washer (ELP 3.5, Biotek, Winooski, Vt.) with PBS-B (10 mM phosphate buffered saline, 0.15 M sodium chloride, containing 0.1% BSA), blocked with 300 μL/well of PBS-B milk (PBS-B containing 5% nonfat dry milk) for 2 h at 37° C. Serum samples were diluted 1:OO in PBS-B milk, added at 100μL/well and rotated at 300 rpm for 1 h. The plates were washed four times with PBS-B and incubated for 1 h with 100 1 μL/well of Biotin-PEG-peptide conjugates (diluted to various concentrations in PBS-B milk).

During this time, the avidin-biotinylated peroxidase complex (ABC) was formed by adding one drop (50 L) of reagent A (avidin DH) and one drop (50 μL) of reagent B (biotinylated peroxidase) to 5 mL of PBS-BT (PBS-B containing 0.5 M sodium chloride and 0.1% Tween 20). The ABC reagent was vortexed and kept at room temperature for at least 30 minutes before use. After washing the plates four times with PBS-B, 7 mL of PBS-BT was added to the ABC reagent and 100 μL of the diluted ABC reagent was-added to each well. The plate was rotated at 300 rpm for 30 minutes and washed four times with PBS-B on the Biotek plate washer followed by two more manual washes with plain PBS. During the last wash, the two component 3,3',5,5'-tetramethylbenzidine substrate solution (TMB) was prepared at room temperature. Substrate was added at 100 μL/well with a repeater pipette (Eppendorf Plus/8), the plate was rotated for 10 minutes to develop the color, and the reaction was stopped by adding 100 μL/well of 1 M phosphoric acid. The plate was then rotated for 2 more minutes to homogenize the color and then read on an ELISA plate reader (Biotek) set for dual wavelengths (450 and 630 nm).

All seven Biotin-PEG-peptide conjugates were tested as antigens in IgM-capture ELISA individually and as in combination with a panel of samples containing sera from both Lyme disease patients and healthy subjects. A group of 12 negative control sera were tested under the same assay conditions and the average absorbance plus three standard deviations of these control serum samples was used as the cutoff.

The index number of each serum sample was calculated as: Index=Absorbance of individual serum/Cutoff. An index number of 1.0 or above is taken as a positive and an index number of 0.8 or below is taken as a negative. Any index number between 0.8 to 1.0 is taken as equivocal.

ii) Clinical Diagnosis by IgM Capture ELISA

A panel of sera is tested by IgM capture ELISA using either protein-based antigen (*Borrelia burgdorferi* sonicate) or our peptide-based antigens. The clinical diagnosis results are listed in Table 2.

The peptide-based ELISA using the combination of seven PEG-peptide conjugates identified 31 positive samples from 33 culture-proven positive samples, resulting in a diagnostic sensitivity of 94% (percentage of disease samples correctly diagnosed). The protein-based ELISA using sonicated *Borrelia burgdorferi* spirochete picked up 23 samples out of 31 tested positive sera, yielding a diagnostic sensitivity of 74%. Furthermore, the peptide-based ELISA did not yield any false positive results with the non-Lyme disease samples giving an essentially 100% of diagnostic specificity, whereas the protein-based ELISA gave 6 false positives out of 23 negative samples, or a diagnostic specificity of 74% (percentage of non-disease samples correctly diagnosed). Thus, the peptide-based ELISA achieved higher sensitivity and specificity than the protein-based ELISA.

As our design rationale predicted, the defined epitope peptides should have less tendency than whole proteins to cross-react with sera from patients with other diseases, such as syphilis. In order to examine this hypothesis further, a panel of serum samples from patients with syphilis infection was tested using the combination of PEG-peptide conjugates (Table 3). Indeed, while 13 out of 25 syphilis samples gave cross-reactive results in the protein-ELISA, none of these tested syphilis samples showed cross-reactivity in our peptide-ELISA when corrected by subtracting serum background (no antigen used in ELISA), indicating that all seven epitope peptides defined in this study are Lyme disease specific and do not cross-react with antibodies against the syphilis spirochete.

SUMMARY

In our claims, we use the singular to include the plural (i.e., "a" or "an" means "one or more").

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the scope of the invention. Thus, for example, serum antibodies specific for any disease can be analyzed in order to select disease-specific epitope sequences. Peptides corresponding to these epitope sequences are then synthesized and conjugated in several copies to a multivalent PEG carrier molecule, along with a reporter group such as biotin. We thus intend the legal coverage of our patent to be defined not by the scientific examples we include here, but by the legal claims appended here.

TABLE 2

Comparison of Lyme disease diagnosis for a panel of serum samples.

| No. | Protein ELISA | Peptide ELISA | Clinical diagnosis | No. | Protein ELISA | Peptide ELISA | Clinical diagnosis |
|---|---|---|---|---|---|---|---|
| MC-2 | P | P | P | NC-1 | P | N | N |
| MC-3(6/18) | N | P | P | NC-2 | N | N | N |
| MC-3(6/26) | P | P | P | NC-3 | N | N | N |
| MC-4 | P | P | P | NC-4 | N | N | N |
| MC-7 | P | P | P | NC-5 | N | N | N |
| MC-8 | N | P | P | NC-8 | N | N | N |
| MC-9 | P | E | P | NC-9 | N | N | N |
| MC-10 | P | P | P | NC-10 | N | N | N |
| MC-14 | P | P | p | NC-11 | N | N | N |
| MC-17 | P | P | P | NC-14 | N | N | N |
| MC-23 | P | P | P | NC-15 | N | N | N |
| MC-33 | P | P | P | NC-16 | N | N | N |
| MC-41 | P | P | P | NC-A | N | N | N |
| MC-59 | P | P | P | NC-B | N | N | N |
| MC-62 | P | P | P | NC-C | P | N | N |
| MO-68 | N | E | P | NC-D | N | N | N |
| MC-70 | P | P | P | NC-E | P | N | N |
| MC-71 | E | P | P | NC-F | N | N | N |
| MC-72 | P | P | P | NC-G | N | N | N |
| MC-73 | P | P | P | NC-H | N | N | N |
| MC-74 | N | P | P | NC-LT | P | N | N |
| MC-91 | N | P | P | NC-LN | P | N | N |
| MC-92 | P | P | P | NC-LP | P | N | N |
| MC-93 | N | P | P | MC-SC | P | P | P |
| MC-100 | N | P | P | MC-EL | P | P | P |
| MO-101 | P | P | P | MC-AN | P | P | P |
| MC-JS | P | P | P | MC-MT | ND | P | P |
| MC-GR | P | P | P | MC-HA | ND | P | P |

P, positive; N, negative; E, equivocal, ND, not determined.

TABLE 3

Comparison of ELISA results for serum samples from patients with syphilis.

| No. | Protein ELISA | Peptide ELISA | Clinical diagnosis |
|---|---|---|---|
| S-1 | CR | NCR | Syphilis |
| S-2 | CR | NCR | Syphilis |
| S-3 | CR | NCR | Syphilis |
| S-4 | CR | NCR | Syphilis |
| S-5 | CR | NCR | Syphilis |
| S-6 | CR | NCR | Syphilis |
| S-7 | CR | NCR | Syphilis |
| S-8 | NCR | NCR | Syphilis |
| S-9 | CR | NCR | Syphilis |
| S-10 | NCR | NCR | Syphilis |
| S-11 | NCR | NCR | Syphilis |
| S-12 | NCR | NCR | Syphilis |
| S-13 | CR | NCR | Syphilis |
| S-14 | NCR | NCR | Syphilis |
| S-15 | NCR | NCR | Syphilis |
| S-16 | NCR | NCR | Syphilis |
| S-17 | NCR | NCR | Syphilis |
| S-18 | NCR | NCR | Syphilis |
| S-19 | CR | NCR | Syphilis |
| S-20 | CR | NCR | Syphilis |
| S-21 | CR | NCR | Syphilis |
| S-22 | CR | NCR | Syphilis |
| S-23 | NCR | NCR | Syphilis |
| S-24 | NCR | NCR | Syphilis |
| S-25 | NCR | NCR | Syphilis |

CR, cross-reactive; NCR, non-cross-reactive.

We claim:

1. A *Borellia burgdorferi* epitope polypeptide with an amino acid sequence comprising SEQ ID NO: 7.

2. The epitope polypeptide of claim 1, wherein said epitope polypeptide consists essentially of SEQ ID NO: 7.

3. A *Borellia burgdorferi* epitope polypeptide with an amino acid sequence comprising SEQ ID NO: 7, wherein an antibody found in a subject with Lyme disease binds to a portion of the polypeptide containing SEQ ID NO: 7.

4. The epitope polypeptide of claim 3, wherein a composition comprises the epitope polypeptide.

5. The epitope polypeptide of claim 3, wherein a kit for detecting Lyme disease in a subject comprises the epitope polypeptide.

6. The epitope polypeptide of claim 3, wherein detecting Lyme disease in a subject comprises determining that said subject produces an antibody that binds to a portion of the polypeptide containing SEQ ID NO: 7.

7. The epitope polypeptide of claim 5, wherein the subject is a human.

8. The epitope polypeptide of claim 5, wherein the kit further comrises a reporter moiety.

9. The epitope polypeptide of claim 8, wherein the reporter moiety is attached directly to the epitope.

10. The epitope polypeptide of claim 8, wherein the reporter moiety is attached directly to an epitope carrier.

11. The epitope polypeptide of claim 8, wherein the reporter moiety is attached both directly to the epitope and to the epitope carrier.

12. The epitope polypeptide of claim 8, wherein the reporter moiety is colloidal metal, carbon black, latex bead, or biotin.

13. The epitope polypeptide of claim 12, wherein the reporter moiety is biotin.

14. The epitope polypeptide of claim 13, wherein the biotin is detected with a spectrophotometer.

* * * * *

SEQUENCE LISTING

<160> NUMBER OF SEQ ID NOS: 7

<210> SEQ ID NO 1
<211> LENGTH: 13
<212> TYPE: PRT

```
<213> ORGANISM: Borellia burgdorferi

<400> SEQUENCE: 1

Val Gln Glu Gly Val Gln Glu Gly Ala Gln Gln Pro
1               5                   10

<210> SEQ ID NO 2
<211> LENGTH: 16
<212> TYPE: PRT
<213> ORGANISM: Borellia burgdorferi

<400> SEQUENCE: 2

Glu Ile Ala Ala Lys Ala Ile Gly Lys Lys Ile His Gln Asn Asn Gly
1               5                   10                  15

<210> SEQ ID NO 3
<211> LENGTH: 15
<212> TYPE: PRT
<213> ORGANISM: Borellia burgdorferi

<400> SEQUENCE: 3

Ile Ser Thr Leu Ile Lys Gln Lys Leu Asp Gly Leu Lys Asn Glu
1               5                   10                  15

<210> SEQ ID NO 4
<211> LENGTH: 11
<212> TYPE: PRT
<213> ORGANISM: Borellia burgdorferi

<400> SEQUENCE: 4

Pro Val Val Ala Glu Ser Pro Lys Lys Pro Glu
1               5                   10

<210> SEQ ID NO 5
<211> LENGTH: 15
<212> TYPE: PRT
<213> ORGANISM: Borellia burgdorferi

<400> SEQUENCE: 5

Asp Lys Lys Ala Ile Asn Leu Asp Lys Ala Gln Gln Lys Leu Asp
1               5                   10                  15

<210> SEQ ID NO 6
<211> LENGTH: 12
<212> TYPE: PRT
<213> ORGANISM: Borellia burgdorferi

<400> SEQUENCE: 6

Ile Thr Lys Gly Lys Ser Gln Lys Ser Leu Gly Asp
1               5                   10

<210> SEQ ID NO 7
<211> LENGTH: 14
<212> TYPE: PRT
<213> ORGANISM: Borellia burgdorferi

<400> SEQUENCE: 7

Gly Met Thr Phe Arg Ala Gln Glu Gly Ala Phe Leu Thr Gly
1               5                   10
```